US006907879B2

(12) United States Patent
Drinan et al.

(10) Patent No.: US 6,907,879 B2
(45) Date of Patent: Jun. 21, 2005

(54) AGENT DELIVERY AND ASPIRATION DEVICE

(75) Inventors: Darrel Drinan, San Diego, CA (US);
Carl F. Edman, San Diego, CA (US);
Robert J. Rosati, Carlsbad, CA (US)

(73) Assignee: NDT, San Diego, CA (US)

( * ) Notice: Subject to any disclaimer, the term of this patent is extended or adjusted under 35 U.S.C. 154(b) by 112 days.

(21) Appl. No.: 10/068,170

(22) Filed: Feb. 4, 2002

(65) Prior Publication Data

US 2003/0145849 A1 Aug. 7, 2003

(51) Int. Cl.[7] .............................................. A61M 11/00
(52) U.S. Cl. ............................. 128/202.22; 128/200.14; 128/200.21; 128/203.12; 128/205.19; 604/35; 604/43; 604/37; 604/319
(58) Field of Search ............................... 604/35, 43, 37, 604/38, 94.01, 403, 317, 319, 327, 311, 294, 212, 216, 217, 218; 606/162; 128/200.14, 200.21, 200.22, 203.12, 205.19

(56) References Cited

U.S. PATENT DOCUMENTS

| | | | | |
|---|---|---|---|---|
| 869,262 A | * | 10/1907 | Pynchon | 604/217 |
| 1,022,601 A | * | 1/1912 | Rumberg et al. | 604/30 |
| 1,469,764 A | * | 10/1923 | Crisenberry | 604/37 |
| 1,526,313 A | * | 2/1925 | Blakeslee | 604/37 |
| 1,856,811 A | * | 5/1932 | Inaki | 604/38 |
| 2,612,894 A | * | 10/1952 | Akins | 604/212 |
| 3,398,743 A | * | 8/1968 | Shalit | 604/36 |
| 3,502,078 A | * | 3/1970 | Hill | 604/94.01 |
| 4,801,292 A | * | 1/1989 | Watson | 604/36 |
| 4,969,578 A | | 11/1990 | Gander et al. | 222/131 |
| 4,998,915 A | | 3/1991 | Hannah | 604/73 |
| 5,301,846 A | | 4/1994 | Schmitz | 222/211 |
| 5,702,362 A | | 12/1997 | Herold et al. | 604/58 |
| 5,713,914 A | | 2/1998 | Lee | 606/162 |

(Continued)

FOREIGN PATENT DOCUMENTS

| | | |
|---|---|---|
| EP | 0 732 111 A2 | 9/1996 |
| EP | 1 051 984 A2 | 11/2000 |
| EP | 1 092 447 A2 | 4/2001 |
| WO | WO 99/49984 | 10/1999 |

OTHER PUBLICATIONS

L. Greiff, U. Pipkorn, U. Alkner and C.G.A. Persson. "The 'nasal pool' device applies controlled concentrations of solutes on human nasal airway mucosa and samples its surface exudations/secretions." Clinical and Experimental Allergy 20:253–259 (1990).

L. Glantz–Larsson, L. Greiff, CGA Persson, M. Andersson. "The nasal pool—device for challenge and lavage of the upper airway of children." Abstract from ICACI 2000 meeting, Sydney Australia, Oct. 15–20, 2000, at http://www.hogrefe.de/Sydney2000/abstracts/P-503.html.

Ear Wash System, Welch Allyn, at www.welchallyn.com.

(Continued)

Primary Examiner—Henry Bennett
Assistant Examiner—Amanda Wieker
(74) Attorney, Agent, or Firm—Knobbe Martens Olson & Bear LLP

(57) ABSTRACT

The methods and devices disclosed provides for the delivery of agents to an orifice cavity and subsequent aspiration of the agent and orifice contents from the orifice cavity and related areas. In one form, the delivery and aspiration system comprises an agent delivery sub-assembly, an aspiration sub-assembly and a device tip sub-assembly. The subassemblies operate to first deliver an agent contained within the device to an orifice cavity and after an optional time delay, subsequently aspirate the delivered agent and orifice contents from the orifice cavity and related areas. In another form, a removable reservoir is provided whereby the aspirated agent and orifice contents from the orifice are assayed either independent of or within the device itself.

7 Claims, 10 Drawing Sheets

SECTION A-A

U.S. PATENT DOCUMENTS

| | | | |
|---|---|---|---|
| 5,806,723 A | 9/1998 | DuBose | 222/211 |
| RE36,070 E | 2/1999 | Ballini et al. | 128/200.14 |
| 5,899,878 A | 5/1999 | Glassman | 604/48 |
| 5,906,198 A | 5/1999 | Flickinger | 128/200.21 |
| 5,910,421 A | 6/1999 | Small, Jr. et al. | 435/19 |
| 6,007,515 A | 12/1999 | Epstein et al. | 604/82 |
| 6,135,358 A | 10/2000 | Ballini | 239/121 |
| 6,145,703 A | 11/2000 | Opperman | 222/82 |
| 6,241,705 B1 | 6/2001 | Ko-Wen | 604/73 |
| 6,291,178 B1 | 9/2001 | Schneider | 435/6 |
| 6,328,718 B1 | 12/2001 | Chiang et al. | 604/319 |

OTHER PUBLICATIONS

Allefree SC2000 Operating Manual, G–intek, Inc.

Bertrand et al. "Temporary nasosinusal drainage and lavage in chronic maxillary sinusitis. Statistical study on 847 maxillary sinuses" Ann. otol Rhinol Laryngol vol. 102, pp. 858–862, 1993.

Burns "Nasal Lavage" J Otolaryngol vol. 21, p. 83, 1992.

Georgitis "Nasal hyperthermia and simple irrigation for perennial rhinitis. Changes in inflammatory mediators" Chest vol. 106, pp. 1487–1492, 1994.

Grosnan "Nasal Irrigation" Laryngoscope vol. 111, pp. 1867–1868, 2001.

Hall and Douglas "Clinically useful method for the isolation of respiratory syncytial virus" J. Infect. Dis. vol. 131, pp. 1–5, 1975.

Masters et al. "Comparison of nasopharyngeal washings and swab specimens for diagnosis of respiratory synctial virus by EIA, FAT and cell culture" Diagn. Microbiol. Infect. Dis. vol. 8, pp. 101–105, 1987.

Ryan–Poirier et al. "Application of Directigen FLU–A for the detection of influenza A virus in human and nonhuman species" J. Clin. Microbiol. vol. 30, pp. 1072–072, 1992.

Schwartz "The Nasal Saline Flush Procedure" The Pediatric Infectious Disease Journal vol. 16, pp. 725–726, 1997.

Shaikh "Ephedrine–saline nasal wash in allergic rhinitis" J Allergy Clin Immunol vol. 96, pp. 597–600, 1995.

Shoseyov et al. "Treatment with hypertonic saline versus normal saline nasal wash of pediatric chronic sinusitis" J. Allergy Clin Immunol. vol. 101, pp. 602–605, 1998.

Tomooka et al. "Clinical study and literature review of nasal irrigation" Laryngoscope, vol. 110, pp. 1189–1193, 2000.

Treuhaft et al., "Practical recommendations for the detection of pediatric respiratory syncytial virus infections" J. Clin. Microbiol. vol. 22, pp. 270–273, 1985.

\* cited by examiner

```
┌─────────────────┐
│ Prime aspirating│── 40
│    assembly     │
└─────────────────┘
        │ Draw agent into
        │ delivery chamber
┌─────────────────┐
│    Actuate      │
│   aspirating    │── 41
│    assembly     │
└─────────────────┘
        │ Deliver agent to
        │ device tip assembly
┌─────────────────┐
│ Deliver agent to│
│ orifice via spray│── 42
│       tip       │
└─────────────────┘
        │ Open check
        │ valves
┌─────────────────┐
│   Vent excess   │── 43
│    pressure     │
└─────────────────┘
        │ Optional
        │ time delay
┌─────────────────┐
│ Apply negative  │
│  pressure to    │── 44
│    orifice      │
└─────────────────┘
        │ Aspirate agent and orifice
        │ contents into device tip
        │ assembly
┌─────────────────┐
│ Store aspirated │
│   agent and     │── 45
│ orifice contents│
└─────────────────┘
```

FIGURE 3

```
┌─────────────┐
│Prime aspirating│── 40
│  assembly   │
└─────────────┘
      │ Draw agent into
      │ delivery chamber
┌─────────────┐
│  Actuate    │── 41
│ aspirating  │
│  assembly   │
└─────────────┘
      │ Deliver agent to
      │ device tip assembly
┌─────────────┐
│Deliver agent to│── 42
│orifice via spray│
│     tip     │
└─────────────┘
      │ Optional
      │ time delay
┌─────────────┐
│Apply negative│── 44
│ pressure to │
│   orifice   │
└─────────────┘
      │ Aspirate agent and orifice
      │ contents into device tip assembly
┌─────────────┐
│Store aspirated│── 45
│  agent and  │
│orifice contents│
└─────────────┘
```

FIGURE 4

SECTION C-C

SECTION B-B

AGENT DELIVERY AND ASPIRATION DEVICE

FIELD OF THE INVENTION

The invention generally relates to an apparatus for the delivery of an agent to an orifice cavity and subsequent aspiration of the agent and orifice contents from the orifice cavity and related areas. More particularly, the invention provides for a single apparatus capable of fluid delivery and subsequent aspiration of the delivered fluids and contents of orifice cavities.

BACKGROUND OF THE INVENTION

Many therapeutic agents require an intravenous route for full potency and efficacy of treatment. Methods utilizing a nasal passageway are preferred to deliver such therapeutic agents under defined conditions. The delivery, through the absorption of the therapeutic agents through the membranes lining the nasal cavity and sinus regions, allows the rapid introduction and dispersion of aerosol or liquid agents. Combined with the ease of use and the relatively few and pain-free side effects, use of nasal passageways is a desirable route of administration.

The delivery of aerosols or liquids into the nasal passages has been described previously. Typically these devices call for the unidirectional delivery of these materials into the nasal passageways. In addition, many devices require the use of positive pressure for the delivery of drugs into the nasal passageways. For example, U.S. Pat. No. 4,969,578 relates to a pressurized dispensing apparatus for nasally administering medicinal products in aerosol form. The apparatus utilizes a pressurized dispensing container which, through positive pressure, dispenses an aerosalized medicinal agent through an outlet valve into the nasal passages of the patient. U.S. Pat. No. 5,906,198 provides for a unidirectional delivery device which utilizes dual air nozzles for spraying mist into the nasal passages of patients. U.S. Pat. No. 6,145,703 discloses a manual multi-dose spray applicator for dispensing a pharmaceutical liquid into the nasal passageways of a patient. As with the previous art disclosed, the '703 patent utilizes a unidirectional positive pressure means for delivering a metered amount of therapeutic agent into a patient's nasal passages.

Delivery of therapeutics in a powder-form to the nasal passageways of a patient is also possible using a positive pressure device. U.S. Pat. No. 5,702,362 ('362) describes a unidirectional nasal application for introducing powdery, pharmacologically active medicaments into the nasal passageways of a patient. The '362 device is similar to what has been described previously, in that positive pressure, supplied through a compressed air source, is used to generate a compressed air jet which transports a metered amount of powdered medicament through an outlet channel into a patient's nose.

Delivery of therapeutics for the reduction of mucus discharge is not without problems and side effects. Over the counter sprays containing allergy or sinus medications often have a wide variety of accompanying side effects, particularly excessive dryness of the nasal passageways.

Delivery of therapeutic aerosol, liquid or powdery agents is not the only use for nasal applicator devices. Devices which utilize larger volumes of liquid to rinse or lavage nasal passageways have been disclosed, and are also useful in the treatment of sinusitis and other nasal inflammatory conditions that require frequent rinsing of nasal passageways to remove foreign bodies trapped or embedded in the nasal cavities. Saline or lavage sprays are also useful in reducing the dryness accompanying sinus or allergy medications. U.S. Pat. No. 5,301,846 discloses a flexible spray bottle for delivery of larger volumes of liquid. The device utilizes a valve which allows air to flow into the bottle, reducing the possibility of secretions from the body cavity being sucked up through the spray opening into the fluid reservoir of the device. U.S. Pat. Nos. 5,899,878 ('878) and 6,135,358 ('358) disclose devices for irrigation of the nasal passageways using pressurized fluids generated from pressurized air containers ('358) or pump delivery devices ('878).

Although the above prior art disclose a means for ravaging or washing nasal cavities or the delivery of therapeutic agents to nasal passageways, one drawback of many devices is the discharge that is created upon dispensing of the solutions. It may be desirable to remove mucus secretions present in the nasal cavities and passageways, either present as a result of an infectious or allergic state, or as a reaction to the administered therapeutic agent. One solution for removing the fluid and mucus present in the nostrils is the use of gravity and physical expulsion of mucus contents. For example, U.S. Pat. No. 5,806,723 ('723) discloses a device to prepare and dispense lavaging solutions into the nasal cavities of a patient. Manual compression of the dispenser bottle, where saline solution is prepared, forces solution from the bottom of the bottle through the outlet tubing and into the patient's nostrils. The '723 patent also discloses a means for postural draining of solution from the nasal cavities. Postural draining is commenced by laying on one's back and holding the head slightly elevated. The process involves deep breathing and removal of expelling mucus as the head is rotated. Mucus removal is inefficient with this procedure, and requires an extensive investment in both time and physical effort. Recent patents have covered the use of outlet/pressure relief ports to both remove and aspirate nasal secretions after washing or lavaging of nasal passageways. U.S. Pat. No. Re. 36,070 ('070) discloses a device for washing nasal cavities which includes a compressed air injector, spray nozzle and a washing liquid. There is also a collection chamber for collecting the discharge arising from washing. However, the collection of this discharge is inefficient in that any forces on the discharge arise from the depressurization of a nasal cavity of unknown volume. The initial pressurization arises from the positive pressure used to form the atomizing spray combined with user technique to close the oral cavity by swallowing. This depressurization arises during the application or administration step. It does not define the volumes collected and does not permit a segregation of the collection step from the application step, thereby limiting the efficiency of the described device. European Patent Application No. 0 732 111 A2 discloses a micronized douche device for cleansing nasal and neighboring cavities. The device discloses an atomizing chamber, utilizing running water pressurized and dispensed with a compressed air injector. The secretions are removed through a discharge port provided at the bottom of the atomization chamber. Although the above invention provides a means for preventing the mixing of cleansing liquid with the cleansing solution that contains the removed secretions, like the '070 patent there is no segregation of the collection step from the application step, limiting the efficiency of the described device. In addition, removal of the cleansing liquid containing nasal cavity secretions is largely performed through gravity of the solution, falling inward into the bottom of the atomization chamber and out through a discharge port.

European Patent Application No. EP 1 051 984 A2 provides for a vacuum means to remove mucus secretions, particularly from infants and others that cannot themselves physically expel mucus. In most situations, however, removal of mucus or nasal secretions is difficult in situations where the mucus or nasal secretions tightly adhere to the walls of the nasal passageways. The '984 patent lacks a means for dislodging or dispersal of such mucus or nasal secretions, making the system ineffective in removing mucus from the nasal passageways of a patient.

There remains a need for the efficient administration of liquids and aerosols to nasal passages and an efficient means for collecting the resulting discharge contained within a single hand-held device.

SUMMARY OF THE INVENTION

The present invention is directed to an apparatus and methods for the delivery of agents to an orifice and subsequent removal of the delivered agent and orifice contents and attached passageways or chambers to the orifice. The invention may also be used as a diagnostic tool for the purposes of ascertaining bodily health.

One aspect of the invention discloses an apparatus for the delivery of an agent to the orifice of an individual. The invention provides for a means to deliver an agent from a first reservoir through a nozzle or other delivery means into the orifice and attached passageways of the individual. After delivery of the agent, the invention provides for a means to subsequently remove said agent and, if desired, orifice contents into a second reservoir contained within the device.

One aspect of the invention discloses an apparatus for the delivery of an agent into an orifice of an individual and the subsequent removal of the agent delivered to the orifice of the individual comprising three sub-assemblies: an agent delivery assembly, an aspirating assembly and a device tip assembly. The agent delivery assembly, which delivers the agent contained within the apparatus to the orifice of the individual, includes a means for generating a positive pressure for delivering the agent and a means for sealably connecting the agent delivery assembly with a device tip assembly. The aspirating assembly, which aspirates the agent and orifice contents from the orifice of the individual, includes a means for generating a negative pressure for aspirating the agent and orifice contents from the orifice, a means for transporting the agent and orifice contents aspirated from the orifice to the storage means contained within the apparatus and a means for sealably connecting the aspirating assembly with the device tip assembly. The device tip assembly, which delivers the agent and removes the agent and orifice contents from the orifice, includes a nozzle means for dispensing the agent received from the agent delivery assembly and aspirating the agent and orifice contents from the orifice, and a means for sealably connecting the device tip assembly with the agent delivery assembly and the aspirating assembly. The orifice is preferably a nose, whereby the agent is delivered to the nasal cavity and associated passageways, and the agent and nasal catarrhal materials are subsequently removed.

Another aspect of the invention provides for a time delay between the delivery of the agent into the orifice of the individual, and subsequent aspiration of said agent and orifice contents from the individual. The time delay may consist of a pilot-operated mechanical means. Alternatively, a timed electrical means coupled to a mechanical valve or other tripping means may be used to delay the aspiration of the delivered agent and orifice contents.

Another aspect of the invention discloses an apparatus for the delivery of a liquid agent to an orifice of an individual. The invention provides for the means to deliver the liquid agent from a first reservoir through a nozzle or other delivery means into the orifice of the individual.

Another aspect of the invention discloses an apparatus for the delivery of a powder to an orifice of an individual. The invention provides for the means to deliver the powder from a first reservoir through a nozzle or other delivery means into the orifice of the individual.

Yet another aspect of the invention discloses an apparatus for the delivery of a mist to the orifice cavity and passageways of an individual. The invention provides for the means to deliver the mist or small volume of fluid from a first reservoir through a nozzle or other delivery means into the orifice cavity and passageways of the individual.

Another aspect of the invention discloses a means for the subsequent re-uptake of a delivered agent into a second reservoir contained within the device. The invention provides for the means to aspirate the delivered agent from the individual for storage within said second reservoir.

Yet another aspect of the invention provides for an apparatus for the delivery of an agent into an orifice of an individual and the subsequent aspiration of the agent and orifice contents from the individual, comprising two sub-assemblies: an agent delivery and aspirating assembly and a device tip assembly. The agent delivery and aspirating assembly, which delivers the agent contained within the apparatus and subsequently aspirating the agent and orifice contents from the individual, includes a means for delivering the agent contained within the agent delivery and aspirating assembly to a device tip assembly, a means for generating a positive pressure for delivering the agent, a means for generating a negative pressure for aspirating the agent and orifice contents from the individual and a means for sealably connecting the agent delivery and aspirating assembly to the device tip assembly, whereby the means for generating a positive pressure and the means for generating a negative pressure are the same. The device tip assembly, which delivers the agent and removes the agent from the orifice of the individual, includes a nozzle means for dispensing the agent received and aspirating the agent and orifice contents from the orifice, a means for connecting the nozzle means with the agent delivery and aspirating assembly, a means for transporting the agent and orifice contents aspirated from the orifice from the device tip assembly to a storage means contained with the apparatus and a means for sealably connecting the device tip assembly with the agent delivery and aspirating assembly.

Another aspect of the invention provides for an apparatus to sample and collect nasal cavity contents for the purpose of ascertaining bodily health.

One aspect of the invention provides for an apparatus to deliver an agent into an orifice of an individual and the subsequent aspiration of the agent and orifice contents from the orifice, whereby the orifice contents removed from the individual is assayed for biochemical, biological or foreign components, comprising three subassemblies: an agent delivery assembly, an aspirating assembly and a device tip assembly. The agent delivery assembly, which delivers the agent contained within the apparatus, includes a means for delivering the agent from the agent delivery assembly to the device tip assembly, a means for generating a positive pressure for delivering the agent and a means for sealably connecting the agent delivery assembly with the device tip assembly. The aspirating assembly, which aspirates the agent and orifice contents from the orifice of the individual, includes a means for generating a negative pressure for aspirating the agent and orifice contents from the orifice, a means for transporting the agent and orifice contents from the device tip assembly to a storage means, whereby the storage means is sealably connected and removable from the apparatus, and a means for sealably connecting the aspirating assembly with the device tip assembly. The device tip assembly, which delivers the agent and removes the agent from the orifice, includes a nozzle means for dispensing the agent received from the delivery assembly and aspirating the agent and orifice contents from the orifice, a means for connecting the nozzle means contained within the device tip assembly and the agent delivery assembly, a means for connecting the nozzle means contained within the tip delivery assembly and the aspirating assembly, and a means for sealably connecting the device tip assembly with the agent delivery assembly and aspirating assembly.

One aspect of the invention provides for a method for the delivery of at least one agent into an orifice of an individual and the subsequent removal of the agent and orifice contents from the individual comprising providing the agent contained within an apparatus for delivery to the orifice, providing a positive pressure means for delivery of the agent to the orifice and providing a negative pressure means for aspiration of the agent and orifice contents from the individual to a storage means contained within the apparatus One aspect of the invention provides a method for the detection of a biological or chemical substance or organism present within an orifice of an individual, whereby an agent is delivered into the orifice of the individual and the agent and orifice contents are subsequently aspirated from the individual, comprising providing the agent contained within an apparatus for delivery to the orifice of the individual, providing a positive pressure means for delivery of the agent to the orifice, providing a negative pressure means for aspiration of the agent and orifice contents to a storage means and assaying of the orifice contents contained within the storage means, whereby the orifice contents are assayed for the presence of a biological or chemical substance or organism.

BRIEF DESCRIPTION OF THE DRAWINGS

These and other objects, advantages and features of the present invention will be more readily understood from the following detailed description of the preferred embodiments thereof, when considered in conjunction with the following drawings;

FIG. 3—Flowchart of operation of the invention in a closed cavity situation.

FIG. 4—Flowchart of operation of the invention in a closed cavity situation.

DETAILED DESCRIPTION OF THE INVENTION

Figure 1:
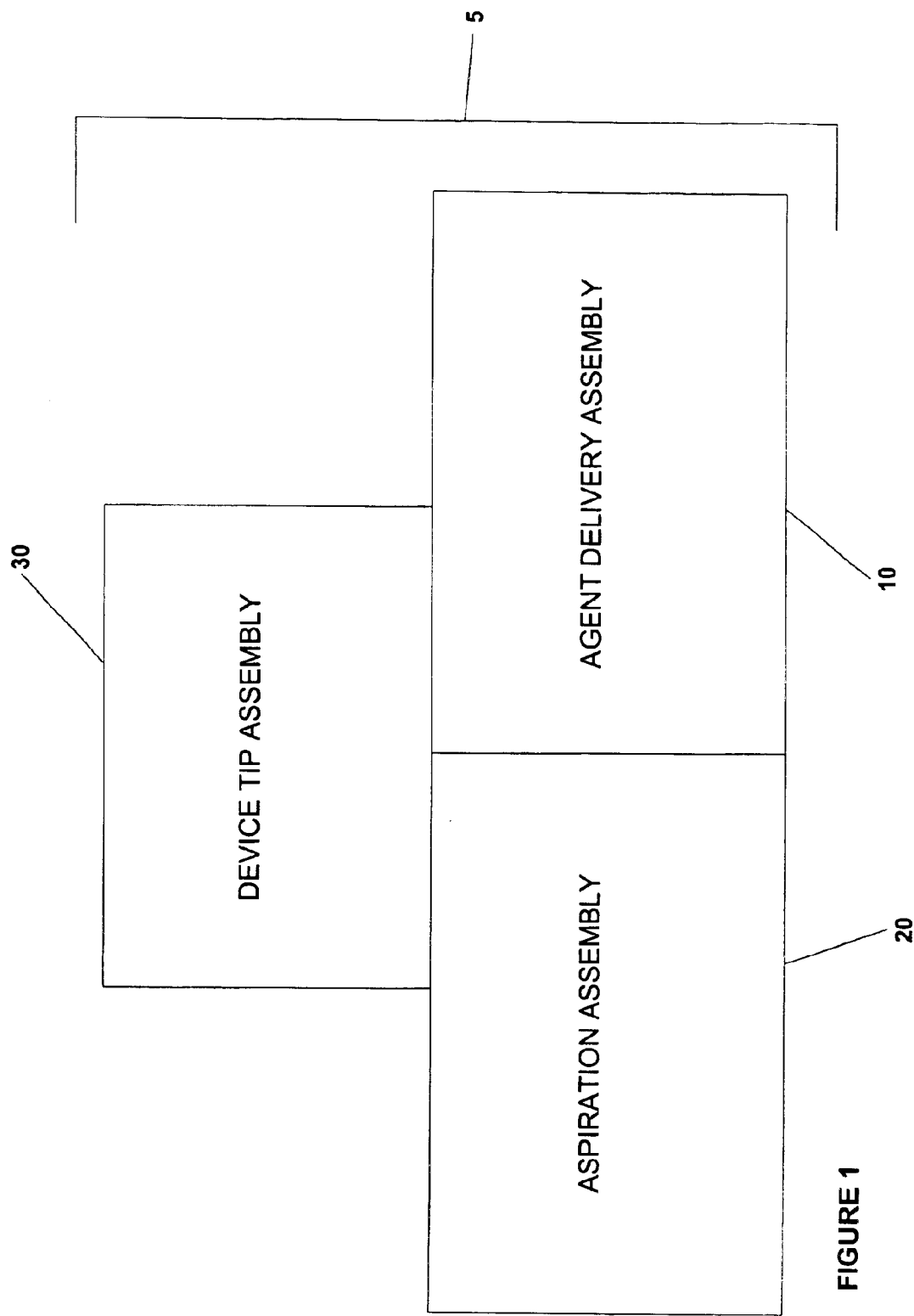
FIG. 1—Diagram of preferred embodiment of the device outlining the agent delivery device, the aspiration assembly and the device tip assembly.

The present invention provides a method and apparatus for the delivery of an agent into an orifice of an individual and the subsequent aspiration of said agent from the orifice and/or neighboring cavities of the individual. An individual is defined as a human or an animal, such as a dog, a cat, a pig, a horse, a sheep, a mouse, a rat, a reptile, a bird, a fish or other animals. An orifice of an individual is defined as structures which are open to the outside environment of the individual. Such orifices may consist of bodily openings, including nasal structures, oral cavity, ear structures, anal structures, vaginal structures and other structures associated with the orifices of an individual. An orifice may also include structures or openings which gain access to internal components or body structures of the individual through an opening in the cutaneous layer. Such orifices may include an incision in the cutaneous layer which creates an opening through which the device may access. Other examples of orifices include structures which permit continued access to the internal components or body structures of the individual, including catheters, portals or other access devices incorporated into an incision made in the cutaneous layer, subcutaneous layer and below such epidermal structures into internal components or body structures of the individual. The invention is not meant to be limiting to orifices in an individual. One skilled in the art may recognize that the device may also be used in conjunction with the delivery of an agent and subsequent aspiration of the agent and contents of orifices not a part of an individuals body, including portals or other access devices to openings within non-organic structures.

The invention, in particular, provides for a means to generate both positive and negative pressure to deliver and aspirate agents to and from the orifice cavity and passageways of the individual. To accomplish this, the invention utilizes a bi-directional flow method to allow for the delivery and subsequent aspiration of agents contained within a single hand-held device. This bi-directional flow can employ one or more nozzles or ports contained within a delivery tip for the dispensation of materials from the device of the present invention into the orifice cavity and passageways of the individual and for the subsequent uptake of fluids and dislodged materials from the same.

The device comprises a platform, which enables a user to deliver solutions or other agents to the orifice, and sequentially retrieve the delivered solution or medicaments and/or any dislodged orifice contents. The described device is flexible, allowing adaptation to the different needs of the various applications described herein.

I. First Embodiment of the Invention

In a first embodiment, the present invention may be used for the delivery of an agent to the orifice cavity and passageways of an individual and the subsequent removal of the delivered agent and/or orifice cavity and passageway contents. An agent, contained within a first reservoir of the device, may be delivered through a nozzle or other delivery device into the orifice cavity and passageways of the individual. Aspiration of the delivered agent and/or any dislodged orifice cavity contents may be sequentially removed and stored in a second reservoir contained within the disclosed device.

A first embodiment of the device is outlined in FIG. 1. The device consists of three major sub-assemblies: the agent delivery assembly 10, the aspiration assembly 20 and the device tip assembly 30. The agent delivery assembly 10 delivers an agent contained within a first reservoir of the subassembly through the device tip assembly 30 to the individual. The aspiration assembly 20, in turn, aspirates the delivered agent and, if desired, orifice contents, from the individual through the device tip assembly 30, storing the delivered agent and orifice contents within the second reservoir contained within the device tip assembly 30, or alternatively, within a second chamber of the device itself 5.

Aspiration Subassembly

Figure 2:
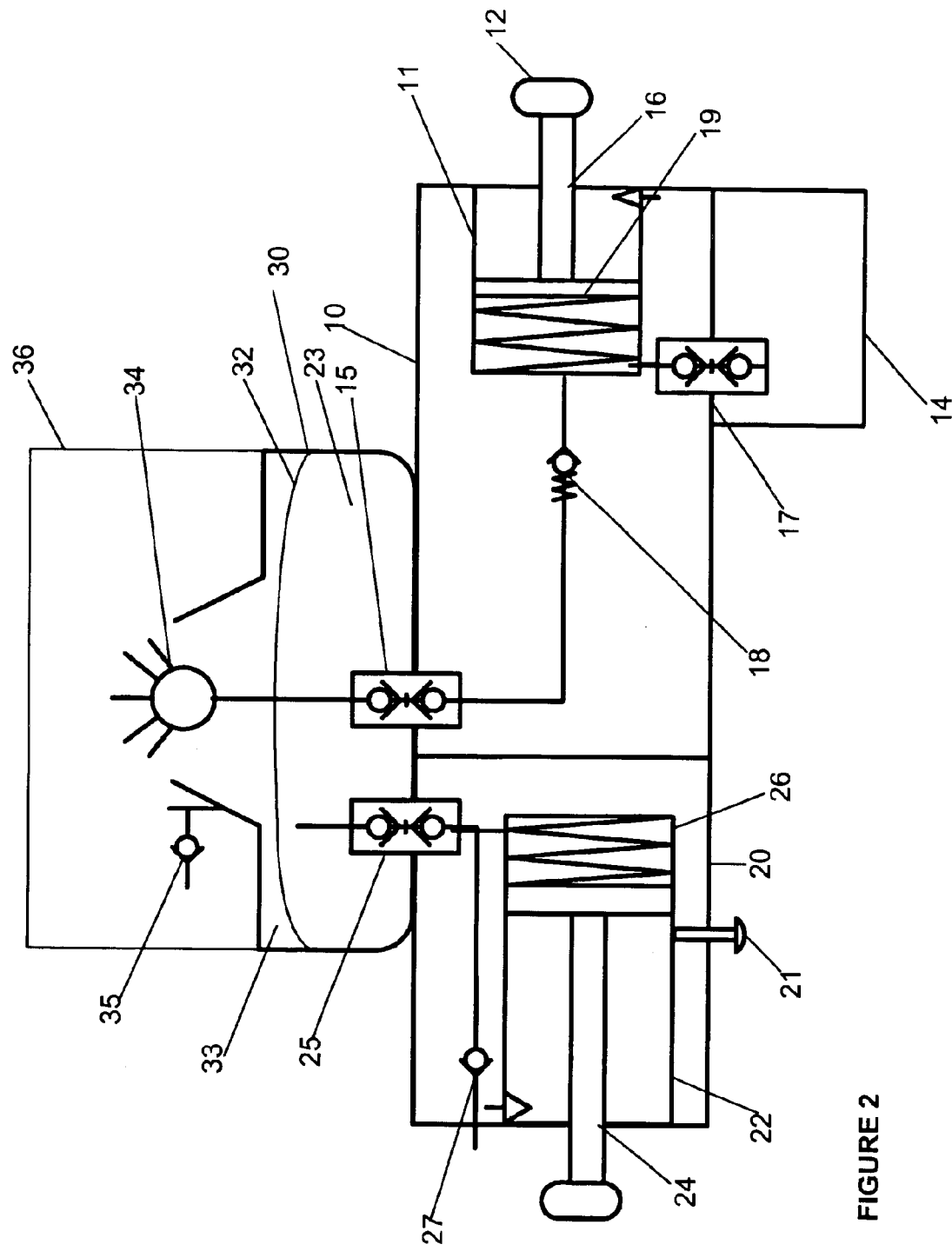
FIG. 2—Detailed drawing of the first embodiment of the invention.

Turning now to detailed drawing FIG. 2 of the first embodiment, the agent delivery assembly 10 portion of the apparatus consists of a base subassembly, whereby said assembly consists of a sprayer pump 11, an agent release button 12, an agent reservoir 14 and a connection assembly 15. The connection assembly 15 allows the sealable connection of the agent delivery assembly 10 with the device tip assembly 30, which contains the ports and nozzles 34 for the dispensation of materials from the agent delivery assembly to the orifice cavity and passageways of the individual. The connection assembly 15 sealably connects the agent delivery and device tip assemblies by clamping the assemblies together via a clamping ring with a suction isolator 32, which forms a flexible seal between the two assemblies. The suction isolator may consist of a filter or membrane sealer, which effectively seals and divides the device tip assembly 30 into two sections.

The positive pressure source utilizes a sprayer pump 11, which is manually operated by the user, generating a source of positive pressure through the withdrawal and return of the delivery piston 16 contained within the sprayer pump. The delivery piston 16 is activated via the agent release button 12 at the bottom of the device. Pressing the delivery piston 16 forces the contents of the delivery chamber containing previously drawn agent from agent reservoir 14, forcing the contents of the delivery chamber out through a check valve 18 to the delivery tip 30. The delivery piston 16 works against a return spring 19 to draw a new volume of agent into the delivery chamber from the agent reservoir 14. In a preferred embodiment, the agent delivery assembly contains an adjustable volume feature, whereby rotating the agent delivery button 12 to different positions sets different volumes of fluid to be delivered. As mentioned above, other means may be used for the generation of a positive pressure source within the agent delivery assembly. Such means include the use of external air cartridges or other mechanical or electrical means which similarly provide a source of positive pressure for delivery of an agent from an agent reservoir 14 to the nasal passageways 36 of an individual. Preferred embodiments of the invention may include the use of removable reservoirs. The removable reservoir may be used for changing or supplying additional materials for dispensing into nasal passages. The removable reservoirs may be composed of solid, porous or flexible materials. Solid materials include, but are not limited to, plastics, metals or glass or combinations of these materials. Flexible materials include, but are not limited to, synthetic resins, natural rubber or latex resins and other flexible plastics or resins.

As mentioned above, agent delivery of an aerosol, mist or fluid stream from an agent reservoir 14 into the orifice cavity and passageways of an individual may employ either a manual or a mechanical means. A manual means may include the use of a hand operated pump or other means to generate an internal positive pressure for delivery of the therapeutic liquids into the nasal passageways. A mechanical means may include the use of preloaded spring assemblies or self-contained chambers having positive pressure relative to ambient conditions. The positive pressure chambers may be the same, or may be contained within a separate chamber from the first reservoir. Alternatively, electrically operated systems and pumps may also be used in conjunction with the present invention to generate a positive pressure necessary for delivery of the agents into the nasal passageways. The electrical means to generate the positive pressure may come in the form of compact battery units, compact fuel-cell systems, solar- or chemically-powered generators, or other means to provide electricity for the generation of positive pressure systems. Alternatively, compressed air cartridges mounted externally to the unit may be used to generate the positive pressure necessary for delivery of the agent into the nasal passageways. In addition, other compressed air sources, such as an external line or feed mounted externally to the device of the present invention, may be used to generate the necessary positive pressure. Yet other alternative means include the use of a chemical reaction contained within or separate from the first reservoir or electrochemical generation or transfer means to generate the necessary positive or negative pressures for delivery or retrieval of the agent.

The agent is preferably a solution, but may also consist of a powder, gel, bead, microemulsion, liposome, micelle or other form. A liquid agent may be delivered as a stream, but may also be delivered as a spray, a mist, a pulsating stream or in another form. Depending upon the application, as outlined below, and state of the orifice cavity, the delivery and aspiration may vary in pressure. The amount of delivered agent may also vary according to the application. For example, rinsing of the nasal passages may require a larger amount of solution, such as 1 milliliter or more. However, delivery of a therapeutic agent may require much smaller amounts, such as microliter or other amounts. The volume of delivered agent may be adjusted in the design depending upon the required application.

The materials may be dispensed as aerosols, micelles, liquids, powders, gels, beads or combinations of these. In an alternative embodiment, the sequential application of materials may be performed, whereby an initial spray of liquid or aerosol is followed by additional applications of other materials. This is especially useful for materials whose storage conditions prevent or limit their combination, e.g. incompatible solvents, buffers or pH, but whose therapeutic value is enhanced by joint application. The sequential application of materials may be performed by the swapping of reservoir or cartridges containing the different materials. Alternatively, the materials may be stored within additional reservoirs, contained within the device.

In some applications, the invention may also include the means to heat materials to be dispensed from the first chamber. This heating may be prior to dispensing or in the action of dispensing. The purposes of this heating may be to aid in pressurizing the device for aiding dispersal, to aerosolize the materials, or to increase the therapeutic value of these materials. This heating may be accomplished by the inclusion of electrical heating elements in order to facilitate this heating process. Alternatively, the heating may be accomplished by the use of microwaves, chemical reaction, external heating, e.g. by immersion in or over hot water, or by the addition of a material or part which has been previously warmed and will heat material in the agent reservoir 14 either prior to dispensing or in the action of dispensing.

Aspiration Subassembly

Once fluid is delivered, it is preferred that the present invention subsequently remove the delivered fluid and/or orifice contents and other discharge or dislodged products. Depending upon the application, fluid and orifice contents may be removed from the individual after delivery of an agent to the orifice cavity and associated passageways. The uptake of delivered agent and subsequently dislodged orifice contents and orifice cavity materials into a storage reservoir may be provided through the generation of a negative pressure means to aspirate delivered materials and orifice contents and dislodged or discharged materials. In a preferred embodiment, a source of negative pressure generation is included within an aspiration subassembly 20 of the device. The aspiration subassembly 20 consists of a vacuum release button 21, a vacuum generator 22, a vacuum reservoir 23, an adjustable valve for release and control of the negative pressure generated 24 and a connection assembly 25, which sealably connects the aspiration subassembly 20 with the device tip assembly 30. A preferred embodiment includes having the negative pressure achieved by mechanical means, i.e. by a pump or other related means. Vacuum generation in general may be achievable through the use of spring-loaded plungers, squeeze bulbs, formed bellows, electromechanical pumps, expanded volumes or the extraction, consumption or condensation of a gas. Alternatively, the vacuum reservoir may have an internal pressure lower than that normally found under general atmospheric conditions as an integral part of the make-up of the vacuum reservoir. For example, the negative pressure may be generated from an additional low pressure container or chamber associated with the device.

In a preferred embodiment, vacuum application is achieved directly after application of the agent to the nasal passageways of the individual. Alternatively, vacuum application may be delayed to allow for the humidification or assist in the dislodging of orifice contents. This delay may be accomplished through manual intervention, by the pressing of vacuum release button 21 by the individual after a desired period of time. The delay may also be accomplished automatically, through the use of a pilot operated delay mechanism. Examples of a pilot operated delay mechanism is the use of a tripping means, whereby vacuum application could be applied by mechanically releasing the aspiration means or by opening a valve that connects between the two. Mechanical release means may include restricting the flow of fluid to refill the agent delivery device 10 and tying the full outward travel of the agent release button 12 to the start of aspiration. Pilot operated delay mechanisms, either pneumatic or hydraulic, are examples of this that are known to those of ordinary skill in the art. Alternatively, the delay may be mediated through a timed electrical operation of a solenoid, motor valve, micromachined valve or the like, which may pneumatically connect the aspiration device to the tip. Any means, mechanical or electrical, which will delay the activation of the aspiration assembly after delivery of agent, may be used in conjunction with the present invention.

Vacuum application and aspiration may be achieved by pressing the vacuum release button 21, which activates the suction piston 24. The suction piston 24 is movably sealed to the suction generator 26 via an O-ring member, but may be sealed with a u-cup diaphragm, a flexible membrane member or any other assembly known to those of ordinary skill in the art. An example of one diaphragm material is heat formable and sealable polyethylene films or film composites. The suction piston 24 in the preferred embodiment works against a spring element during cocking and is latched into the generator housing 26 prior to activation. Air displaced during cocking of the suction piston 24 escapes through a check valve 27 or through a suction isolator 32, keeping the cavity at atmospheric pressure for ready suction generation. Activation of the vacuum release button 21 allows the spring to work against the plunger 24 to expand the suction cavity volume to lower the internal pressure. Assuming a low friction of the suction piston action upon activation, the force of the pressure difference across the piston area reaches equilibrium with the spring force of the spring element. The maximum desired suction pressure may thus be chosen by evaluating the spring force of the spring element, as well as the piston geometry and efficiency of the seals.

The aspiration subassembly may not require a separate source of vacuum generation means. Alternatively, the negative pressure may be coupled to the initial generation of positive pressure associated with dispersal of materials from the first reservoir. Specifically, the expansion of the first chamber of the disclosed device is linked to the forming of a negative pressure in a second reservoir. Alternatively, the first and second reservoir may be contained within one and the same chamber. In yet another alternative, the negative pressure may be independent from the dispensation of materials from the first reservoir.

Device Tip Assembly

Delivery of the agent contained within the agent delivery subassembly 10 and aspiration of the agent and orifice contents from the orifice interface through the device tip assembly 30. Within the device tip assembly 30, delivery of the agent received from the aspiration assembly 10 is through a nozzle 34, whereby the nozzle is capable of delivering the agent in different forms, including as a spray, stream, mist, powder or other forms known to those of skill in the art. Storage of the agent and orifice contents aspirated after delivery of the agent may be within the device tip assembly in storage chamber 33. Alternatively, storage of the agent and orifice contents aspirated after delivery of the agent may also take place within a second reservoir of the disclosed device. A check valve 35 may vent the storage chamber 33 and the device tip 30 to regulate pressure applied to the orifice cavity 36.

In a preferred embodiment, the nozzle 34 comprising the dispensing and uptake ports contained within the device tip assembly 30 snugly fit within the orifice opening, forming a temporary seal from the orifice passageways to the outside of the device. This prevents the leakage of materials during delivery and improves the positive and negative pressure generation capabilities for delivery to and aspiration from the orifice cavity and passageways.

The amount of positive pressure necessary for delivery of solutions to the nasal passageways is directly dependent upon the condition of the orifice cavity. For example, the nasal cavity may be in one of three states: closed, restrictively vented to atmosphere or freely vented to atmosphere. Injected volumes and rates of delivery necessary to generate excessive pressure will depend on the cavity state. The present invention compensates for variations in nasal cavity states and adjusts the amount of pressure utilized for delivery of fluids. Preferably, the user or other party may manually adjust the amount of pressure necessary depending upon an assessment of the nasal cavity state of the individual. This may occur through the manual adjustment of the delivery pressure and/or through changes in the amount of venting to the external environment. Alternatively, the device of the present invention may automatically compensate for the nasal cavity state of the individual by measuring the amount of pressure-buildup within the nasal cavity and adjusting the delivery pressure or venting state utilized. In this embodiment, pressure sensing devices may be mounted on the tip of the device or any other suitable location allowing the automatic sensing and subsequent adjustment of delivery pressure or change in venting of the present invention to the external atmosphere.

As stated above, the amount of positive pressure necessary for delivery of an agent to the nasal passageways is directly related to the condition of the nasal cavity. For example, a nasal cavity plugged both inwardly by swollen tissues and externally by the devices delivery tip may build excessive pressure and uncontrollably vent past the delivery tip upon injection of fluid or agent. FIG. 3 outlines the events that may occur upon delivery and subsequent aspiration of an agent and nasal contents using the present invention. The aspiration assembly is primed 40, after which agent is drawn into the delivery chamber of the aspiration assembly. The aspirating assembly is actuated 41, after which a positive pressure is generated delivering the agent to the orifice through the device tip assembly 42. Due to the closed state of the nasal cavity, the pressure of the cavity, and consequently the apparatus, is increased after delivery of the agent. For subsequent aspiration of the agent and orifice contents, the cavity is first vented to the external atmosphere 43 by opening check valves, or other valve or vent structures, within the device tip assembly or other structure within the device. After an optional time delay, negative pressure is applied to the orifice 44 through the generation of a negative pressure force, aspirating agent and orifice contents into the device tip assembly. The aspirated agent and orifice contents are stored within the device 45.

An alternative means for venting the nasal cavity to the external atmosphere is to insert an internal vent into the collection cavity of the present invention. This collection cavity is either part of that used when collecting the fluid with suction or separated depending on the end desire and disposition of the fluid collected. Gas displaced from this cavity is either vented external to the device or through a check valve. This check valve is of low cracking pressure unless it is desired to slightly pressurize the cavity. Another means that may be utilized is to adjust the delivery pressure of the device to avoid build-up of excessive pressure into the nasal cavity. Alternatively, the device may compensate for excessive pressure build-up by alternating delivery of the agent through a positive pressure means followed by venting of the nasal cavity and device to the external environment, repeating until sufficient amounts of agent is delivered to the nasal cavity.

A nasal cavity restrictively vented to the atmosphere may not build-up threshold levels of pressure upon delivery of fluid into the nasal cavity. In this state, a nasal cavity may require minimal positive pressure delivery control, or may require minimal to no external venting to decrease any built-up excessive pressure as a result of delivery of fluid into the nasal cavity. A nasal cavity which is freely vented to the atmosphere may not require precise control of delivery pressure as a result of the lack of pressure build-up upon agent delivery. FIG. 4 outlines the events that may occur upon delivery and subsequent aspiration of an agent and nasal contents using the present invention. The aspiration assembly is primed 40, after which agent is drawn into the delivery chamber of the aspiration assembly. The aspirating assembly is actuated 41, after which a positive pressure is generated delivering the agent to the orifice through the device tip assembly 42. Due to the open or restrictively vented state of the nasal cavity, the pressure of the cavity, and consequently the apparatus, may not be increased after delivery of the agent. No venting may be necessary, and after an optional time delay, negative pressure is applied to the orifice 44 through the generation of a negative pressure force, aspirating agent and orifice contents into the device tip assembly. The aspirated agent and orifice contents are stored within the device 45.

However, cavities which are freely vented to the atmosphere still require some form of control in order to prevent excess fluid from entering beyond the nasal cavity area into the inner-ear chamber or other chambers intertwined or otherwise connected with the nasal passageways.

The level of positive pressure necessary for delivery of agent, however, may also be dependent upon the particular application of the device. Depending upon the application, the necessary levels of delivery pressure may be large or small and may be adjusted manually by the individual or other person, or automatically set according to the desired application. In applications where delivery of small amounts of an agent to the external nares or passageways is performed, high levels of positive pressure generation may not be necessary. For example, delivery of therapeutic agents into the nasal passageways may require the delivery of small amounts of agent into an area relatively close to the external nares or passageways of the individual. Conversely, applications which require the delivery of larger amounts of an agent to an internal portion of the nasal passageways may require the generation of higher levels of positive pressure for adequate delivery. Similarly, applications which require only agent delivery may not require the generation of high levels of positive pressure, as compared to applications, such as rinsing or lavaging of the nasal passageways, which require the dislodging of nasal catarrhal or other nasal passageway contents in addition to the delivery of agent to the nasal passageway. Where dislodging of nasal catarrhal contents is required, the requirement for the generation of positive pressure may also vary, depending upon the amount of nasal contents to be removed or the degree of adhesion of the nasal contents to the cavity itself. Therefore, the level of positive pressure generation necessary may be dependent upon the end application, and evaluation of both the application as well as nasal cavity state may determine the amount of positive pressure necessary for the particular individual's situation.

The level of negative pressure necessary to adequately remove nasal contents is dependent upon the end application as well as the state of the nasal cavity. In one case, the application may require sufficient negative pressure (and high pressure differentials) to remove dislodged nasal materials along with delivered nasal therapeutic agents. In an opposite scenario, the application may require removal of available fluid at the delivery tip so as to limit leakage of contaminated materials. An in between case is when collection is desired at an intermediate level of vacuum. Similarly, the state of the nasal cavity of an individual affects the amount of negative pressure generated by a given output in mechanical energy. For example, maximum suction would be created when sealing the device and generating a negative pressure in a low volume, closed cavity, i.e. a congested nasal cavity. In the opposite spectrum, high levels of suction would be difficult to generate in a nasal cavity which is freely vented to the atmosphere. Vacuum generation will thus vary according to the type of application of the device and the pressure differentials required of the differing applications.

One means of controlling the level of vacuum generated is to alter the tip design. By varying the type of venting control available with various tip designs, the device may provide the control necessary to achieve the required amount of negative pressure to fit the application. For example, a simple trough vent on the outside of the delivery tip could serve as the vent to allow air in for residual fluid collection. By providing alternative tip designs which vary the amount of venting, the generation of only one level of negative pressure is required for sufficient control and removal of a delivered agent and/or nasal passageway contents. A high cracking pressure check valve may be used for the intermediate case. Vents are placed so that external air must first enter the cavity thus allowing the cavity contents to be displaced. Where maximum pressure differentials are necessary, no vent may be needed for the generation of maximum pressure differentials necessary for the generation of the required amount of vacuum. By providing alternative tip designs which vary the amount of venting, the generation of only one level of negative pressure is required for sufficient control and removal of a delivered agent and/or nasal passageway contents. Alternatively, use of varying tip designs combined with the control of the amount of negative pressure generated may also be utilized to vary the amount of vacuum generated for each application. Similarly, control of the amount of the negative pressure generated may alone sufficiently control the generation of the negative pressure depending upon the application, such that no alternative tip or venting designs are necessary.

II. Second Embodiment of the Invention

One application of the invention is the use of the device for the rinsing and lavaging of the nasal passageways, and the subsequent removal of the lavage solution and/or nasal cavity contents which are dislodged as a consequence of the lavaging action. This will provide relief and removal of irritants, such as pollen or other allergens from the nasal passageways. Rinsing of nasal passageways and removal of irritants may relieve any inflammation of the membranes lining the sinuses and nasal cavities, which may or may not be accompanied by a bacterial infection. Rinsing of nasal passageways may also circumvent the need for medicinal compounds or other therapeutics traditionally used in the treatment of sinus or nasal cavity inflammation.

Solutions which aid in the rinsing and removal of nasal catarrhal materials are preferred. These materials, which are contained within the agent reservoir, may include, but are not limited to, water, saline solutions, or other solutions used by those of ordinary skill in the art for the rinsing or lavaging of membranes lining the nasal cavity or sinuses of a patient.

Nasal Rinse and Lavage System

A nasal lavage device encompassed by the present invention may take a variety of forms, depending upon the volume and state of the nasal cavity, as well as the volume of the agent necessary for efficient lavaging of the nasal passageways. The latter element is largely dependent upon the size of the individual. For example, a smaller individual (e.g. baby, toddler, child or smaller adult) requires approximately 1.0 ml of lavage solution for the efficient rinsing of the nasal passageways. Larger individuals (e.g. larger children or adults) require correspondingly larger amounts of lavage solution (approximately 2.5 ml or more) for the efficient rinsing of the nasal passageways. In order to compensate for the variations in liquid volumes required for efficient lavaging, the device of the present invention provides for the ability of the user to vary the volumes required, either through manipulation of the volume of fluid delivered, or through the manipulation of the volumes present within the first reservoir of the device for delivery to the nasal passageways.

Figure 5:
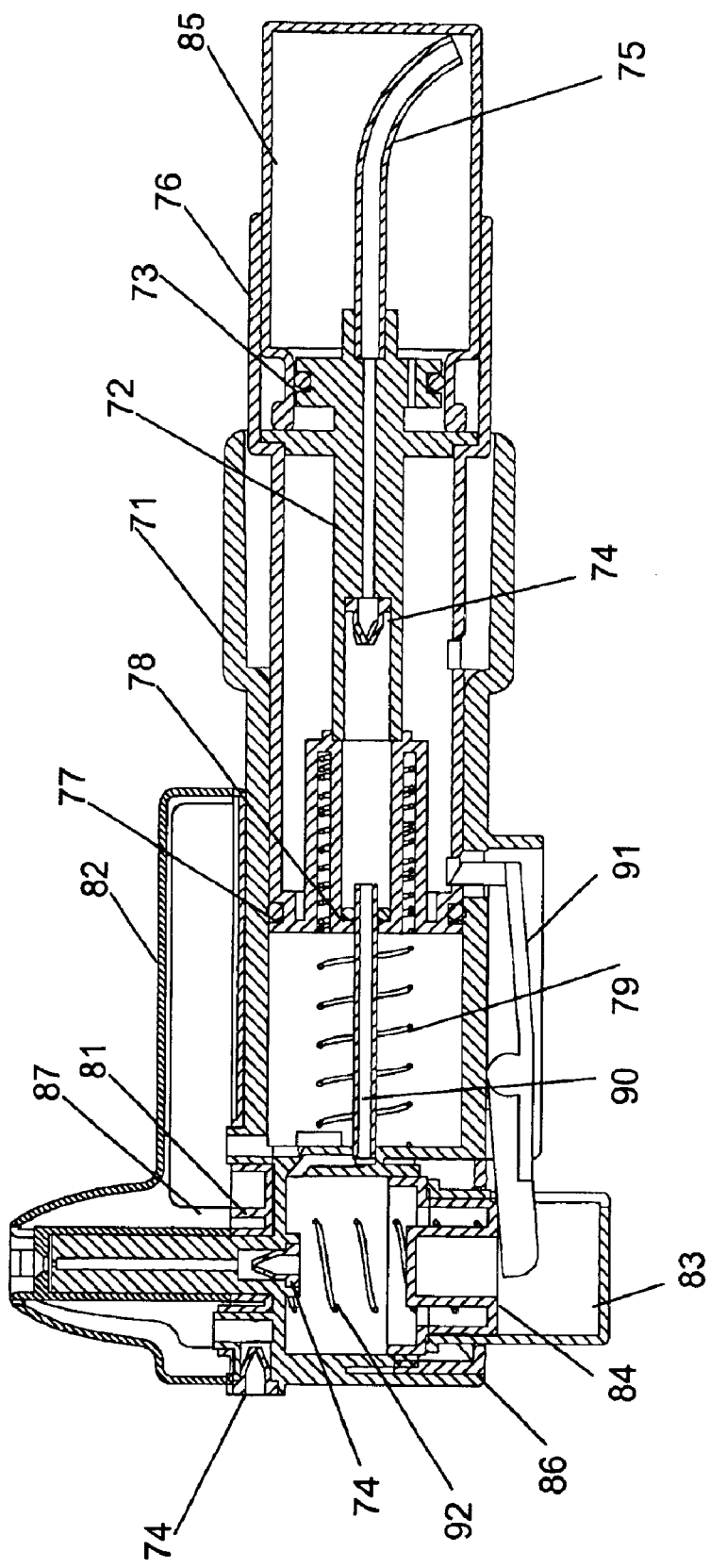
FIG. 5—Cross sectional detailed drawing of the invention for use in lavage or washing of the orifice cavity.
Figure 6:
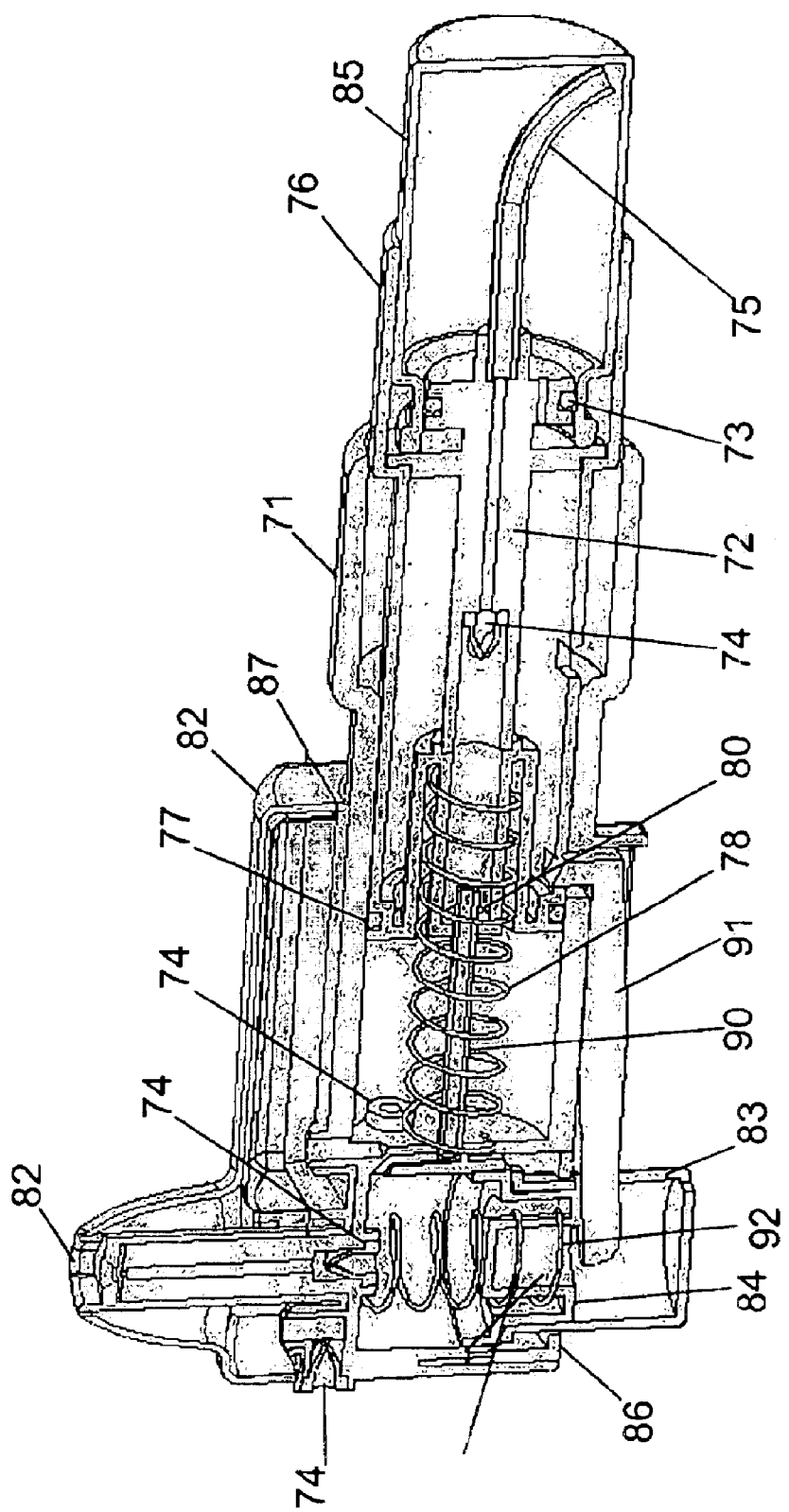
FIG. 6—Cross sectional detailed drawing of the invention for use in lavage or washing of the orifice cavity.

FIGS. 5 and 6 depicts a device for use in the lavaging of the nasal passageways of an individual. The device encompasses all features recited in the above first embodiment of the invention. In the device, first reservoir 85 filled with agent is attached into plunger 76 and seals thru seal 73 to bottle plug 72. The fluid path is primed by depressing squirt plunger 83, flexibly or slideably sealed by 84, which forces air out spray tip via associated first check valve duckbill 74. There are four check valves in this device. Releasing the squirt plunger 83 allows the spring 92 to push the squirtplunger back out which aspirates agent from bottle 85 thru takeup tube 75 into bottleplug 72, thru second duckbill 74, thru agent tube 90 and associated path in body 71 into squirting chamber.

Once primed the device is cocked so it can generate a vacuum suction force. Plunger 76 assembly, sealed by seal 78, is pushed into body 71, displacing air out third check valve 74 mounted thru end face of chamber. Hole in wall of plunger 76 is caught by catchhook 91 when plunger 76 is fully depressed in body 71. Depressing squirtplunger 83 releases agent thru spray tip. During squirt plunger 83 depressions, if the flushed cavity is blocked, agent will immediately flow into the collection reservoir 82 and displace air thru third check valve 74. At the end of the travel, the squirtplunger 83 trips catchhook 91 to release plunger 76. Plunger 76 is pushed back by spring 79 lowering the pressure in the cavity formed by its movement and the cavity in the collection reservoir fluidly connected to it. The lowered pressure compels materials at the tip of the orifice interface unit to be drawn into the collection reservoir thru internal pathways. If the flushed cavity (nasal cavity) is blocked then outside air is drawn thru fourth check valve 74 into separate channel and out a separate hole at the tip of the orifice interface unit. A serial path is formed to allow air into the closed cavity (nasal cavity) so that agent can be displaced via the lowered pressure. Vacuum generator isolator, labeled diaphragm 87, is either displaced as fluid enters if it is impermeable or acts as an air only filter.

The removable collection reservoir is sealed to the body 76 at three ports by the nature of the materials/fits or by separate seals (seals not shown).

Elastic Bulb System

Figures 7A, 7B:
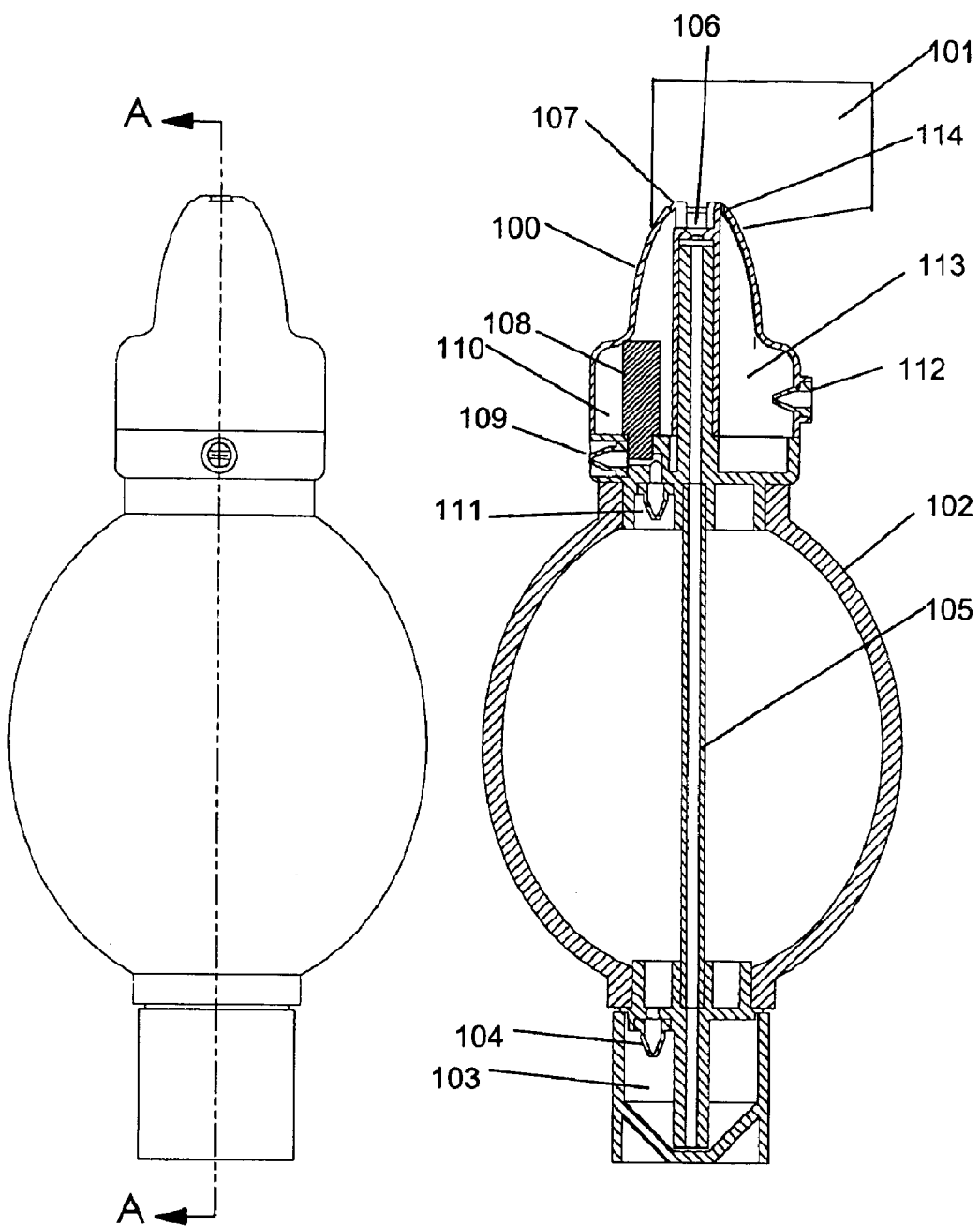
FIG. 7—An elastic bulb form of the invention. A. Outside aspect view of an elastic bulb form of the invention. B. Cross-sectional view of an elastic bulb form of the invention.

Alternatively, the nasal rinse or lavage system may incorporate an aspirating sub-assembly and agent delivery sub-assembly into one piece, whereby the generation of positive pressure and negative pressure is accomplished through one device. FIGS. 7A and 7B exemplifies this embodiment of the invention. Held upright as shown delivery tip 100 is sealably inserted into the orifice cavity 101. Elastic bulb 102 is squeezed, increasing the internal pressure and forcing contained gas in the device into lower reservoir 103 through valve 104. Lower reservoir 103 contains agent to be delivered to the orifice cavity 101. Gas pressure from the squeezing of elastic bulb 102 forces agent contained in lower reservoir 103 up center agent path 105 and out delivery nozzle 106. Excess gas pressure created from expelling agent into the orifice cavity 101 is vented through collection port 107, filter 108 and out valve 109 at a predetermined pressure. The internal pressure generated, and subsequent negative pressure applied, may be adjusted either through the selection of materials (e.g. varying the elasticity of the bulb apparatus), or through the use of valves or other devices to regulate the amount of depression of the bulb and subsequent decrease in the amount of displaced air into the lower reservoir 103.

Aspiration of agent and orifice contents from the orifice cavity 101 is accomplished by releasing elastic bulb 102, which closes valve 104 and draws contents from cavity through the collection port 107 and into the collection reservoir 110. Filter 108 allows gas to pass, but not fluid, through valve 111 and into elastic bulb 102. If the orifice cavity 101 is internally vented and open, gas may be drawn from the same. If the cavity is plugged and closed, air is drawn through valve 112 into segregated path 113 and out opening 114 into the orifice cavity 101. With air displacing contents of the cavity, the orifice contents can be collected in reservoir 110.

Figures 8A, 8B:
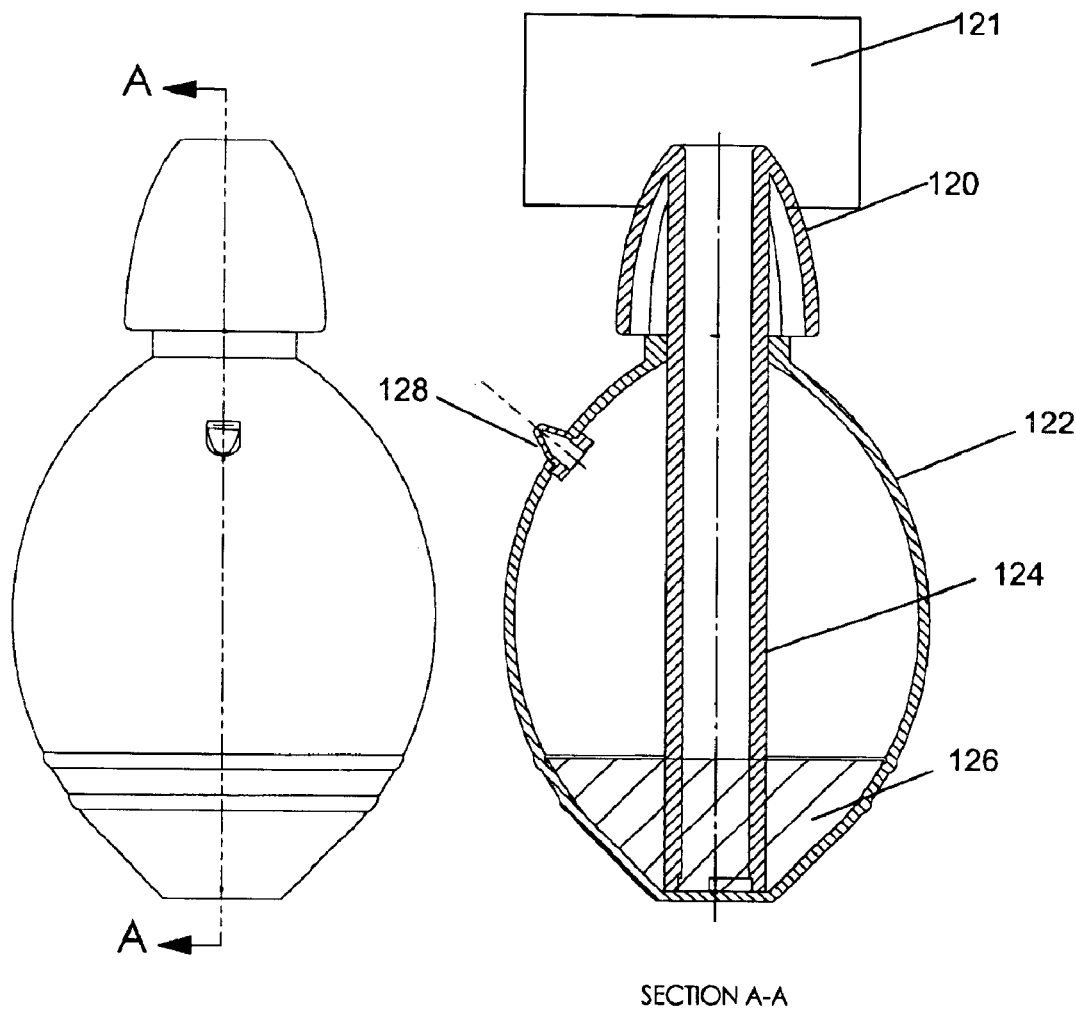
FIG. 8—An alternative elastic bulb form of the invention for use with a closed cavity. A. Outside aspect view of an alternative elastic bulb form of the invention. B. Cross-sectional view of an alternative elastic bulb form of the invention.

An alternative device also includes the use of the elastic bulb system, whereby the agent storage reservoir and the aspirated orifice contents reservoir are the same. In this embodiment, seen in FIGS. 8A and 8B, the nasal rinse or lavage system may again incorporate an aspirating subassembly and agent delivery sub-assembly into one piece. In FIG. 8B, held upright as shown, delivery tip 120 is sealably inserted into orifice cavity 121. Elastic bulb 122 is subsequently squeezed, increasing the internal pressure of the device and forcing agent contained in reservoir 126 into the delivery/aspiration tube 124 to delivery tip 120. The end of the device tip assembly 120 is shaped to funnel agent to voids at the end of tubing 124. Once agent is delivered to the orifice cavity 121, gas above the agent is bubbled into the orifice cavity 121 to increase the mixing of the agent within the cavity. After a fixed amount of agent is delivered, if the cavity is plugged and closed to pressure above a preset pressure, valve 128 may vent excess gas and pressure which allows a large volume aspiration to still occur if the plug responds to vacuum pressure. Vacuum pressure may be applied to the orifice cavity by releasing the elastic bulb 122, which closes valve 128 and creates a negative pressure in elastic bulb 122, aspirating materials at delivery tip 120 into bulb 122 through delivery/aspiration tube 124.

Figure 9A:
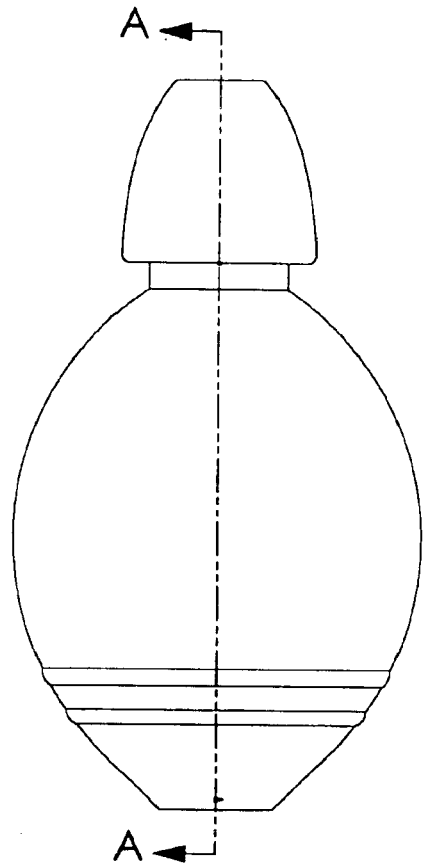
FIG. 9—An alternative elastic bulb form of the invention for use with an open cavity. A. Outside aspect view of an alternative elastic bulb form of the invention. B. Cross-sectional view of an alternative elastic bulb form of the invention.
Figure 9B:
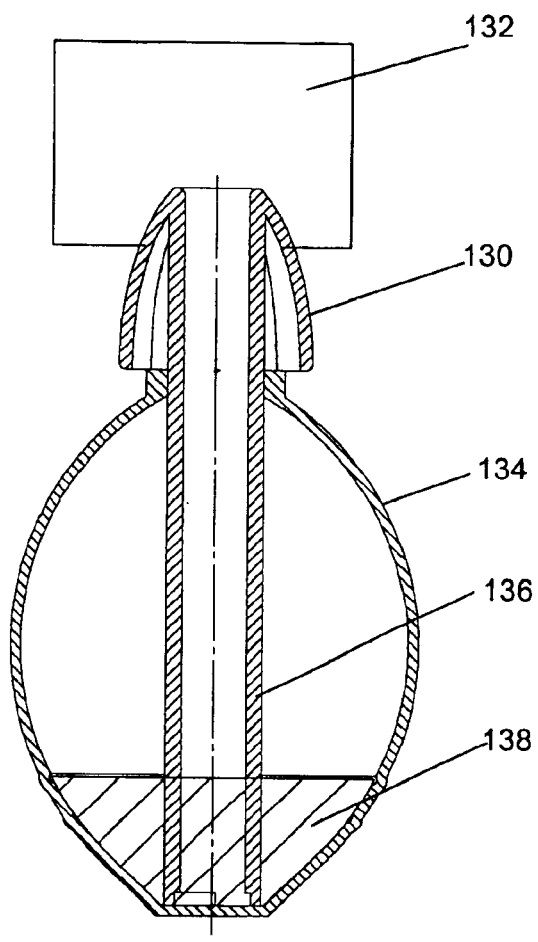

Yet another device may also incorporate an aspirating sub-assembly and agent delivery sub-assembly into one piece. As seen in FIGS. 9A and 9B, the device does not include any pressure relief valves and may be used in situations where the cavity is internally vented and open. Held upright as shown, the device in FIG. 9B may be sealably inserted into orifice cavity 132 via device tip 130. Elastic bulb 134 is squeezed, which increases internal pressure and forces agent contained within reservoir 138 into delivery/aspiration tubing 136 to device tip 130. The end of the device tip 130 is shaped to funnel agent to voids at the end of tubing 136. Once the agent is delivered to the orifice cavity 132, gas above agent is bubbled into the cavity to increase mixing. To aspirate orifice contents, elastic bulb 134 is released, creating negative pressure in elastic bulb 134 aspirating materials at device tip 130 into elastic bulb 134 through delivery/aspiration tubing 136.

III. Third Embodiment of the Invention

Yet another aspect of the invention is the use of the device for the delivery of therapeutic agents, medicaments or other agents. The device of the present invention may be used to deliver smaller volumes of agents into an orifice cavity and passageways of an individual user, and the subsequent aspiration of said delivered therapeutic agents. Aspiration of the delivered agents may alleviate backflow or nasal drip, which commonly occurs after delivery of fluidic agents. By doing so, the device may also decrease the spread of contamination of infectious agents contained within said backflow or nasal drip by confining nasal contents or infectious agents to the device of the present invention. When delivering small volumes it may be required to deliver in a mist form. In this case the device delivers a quantity of air adjacent to or into the fluid pathway to atomize the agent and also to carry it into the cavity recesses. Typically this is done through small openings to achieve high velocities. Small openings may not be beneficial for aspiration of the resulting discharge products or other orifice contents. A flap valve at the tip would respond to the negative pressure in the collection cavity and open a larger opening to collect the materials at the tip. Alternatively, a squeeze bulb type device could apply a negative pressure to the end of the delivery tube and be the source of the extra airflow to open the flap valve for subsequent collection of the aspirated orifice contents. Solutions containing therapeutic agents, such as antihistamines, decongestants, antibiotics, vasoconstrictors, anti-inflammatory agents, vaccines, biological agents, such as genetic-based therapies or cellular or organism-based therapies, and/or solutions containing diagnostic agents or materials and other agents known to those of ordinary skill in the art may be used in conjunction with the present invention.

Use of the Invention in the Delivery of Small Volumes of Therapeutics

Figure 10A:
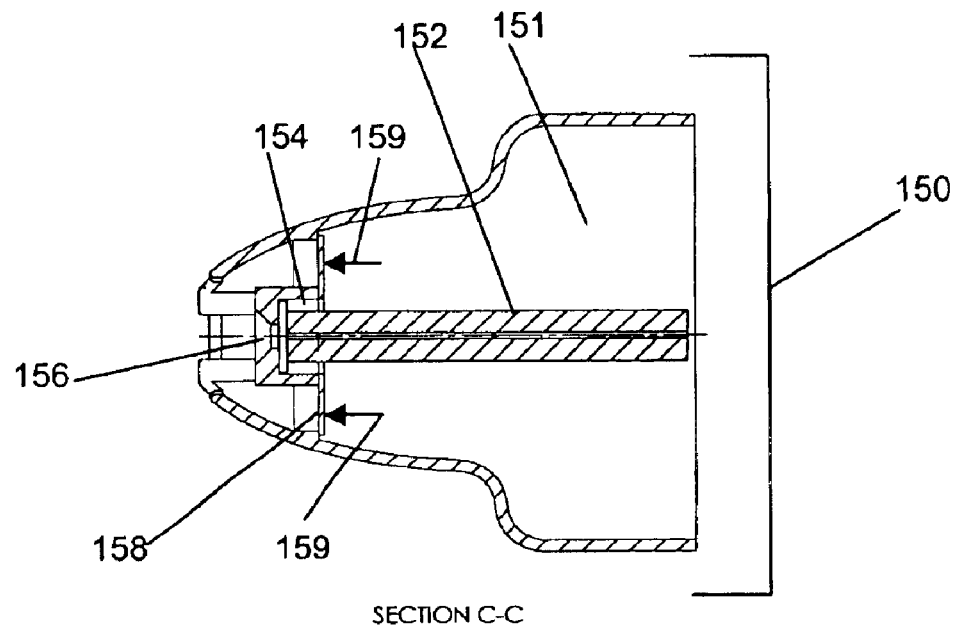
FIG. 10—Detailed drawing of an atomization device. A.—Operation of the device upon actuation of the agent delivery assembly. B.—Operation of the device upon activation of the aspirating assembly.
Figure 10B:
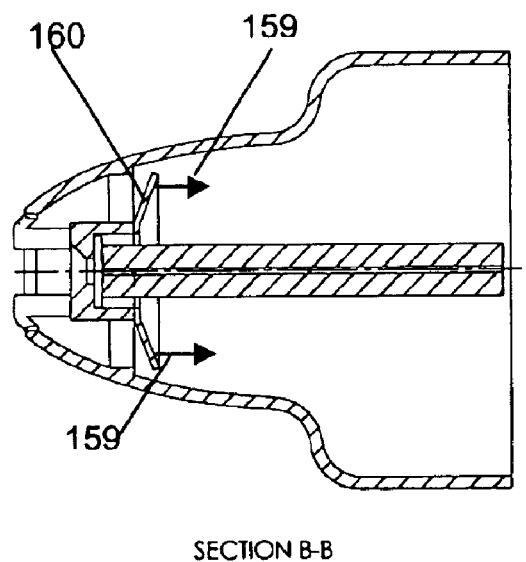

When delivering smaller volumes of liquids or fluids, delivery in a mist form may be required. For generation of a mist, the device may deliver a quantity of air adjacent to or into the fluid pathway to atomize the agent and also to carry in into the cavity recesses. It is well known in the art that this may be accomplished through the passing of the agent through small openings to achieve high velocities. FIGS. 10A and 10B illustrate an example of a mist generator in conjunction with the tip delivery assembly 150 of the invention. In the drawing, a mist may be generated by forcing agent up pathway 152 through the generation of positive pressure forces as discussed previously. The agent in pathway 152 is mixed with air bypassing flapper 158 through port 154 and around end of tube to exit 156. Flapper 158 is held closed when agent is expelled from the tip delivery assembly, as demonstrated by arrows 159 in the device. Alternatively, atomization of an agent may also occur through atomization devices commonly known to those of skill in the art. These include e.g. ultrasonic horns or piezo-electric benders, and inkjet or piezojet nozzles. The agent could also be volatilized off a flash heated surface and carried by an air jet into the cavity.

However, small openings may not be beneficial for aspiration of the resulting discharge products. Larger discharge products or orifice contents may be trapped within the small openings of device tip assembly 150 and clog the device. A flap valve at the tip may circumvent this clogging by diverting resulting discharge products and orifice contents through a larger opening, storing the aspirated discharge products and orifice contents in reservoir 151. In operation, the device may open flapper valve 160 after delivery of agent by lowering the pressure in device tip 150. By opening the flapper value, agent and discharge recovery may occur through the larger ports. If, however, an atomization device is used which atomizes an agent prior to the device tip nozzle, whereby small openings are not necessary for the atomization of the agent, the flap valve structure may not be necessary for collection of aspirated products from the orifice cavity and passageways.

III. Fourth Embodiment of the Invention

The device may also be used for the collection and sampling of orifice contents for the purpose of ascertaining bodily health. A preferred application for this embodiment of the invention is the delivery of an agent from a first reservoir is followed by aspiration of the delivered agent along with dislodged nasal contents from the nasal passageways. Alternatively, fluids, such as applied agents, interstitial fluids, vascular fluids, mucosal fluids or discharge and ductual fluids, tissues, cellular materials or samples or gaseous contents from an orifice may also be collected. Aspiration is collected in a removable second reservoir, after which testing of the reservoir contents for a target is performed. Examples of a target include metabolites, chemical, organic or inorganic compounds or elements, foreign particulate matter, microbial pathogens or other pathogens, organisms or compounds and other targets known to those of ordinary skill in the art which are known to assist in ascertaining the individuals health status. Alternative applications may include an assay means within the device to test for the presence of metabolites, chemical, organic or inorganic compounds, or elements, foreign particulate matter, microbial pathogens or pathogens, organisms or compounds. The removable reservoir may be composed of solid, porous or flexible materials. Solid materials include, but are not limited to, plastics, metals or glass or combinations of these materials. Flexible materials include, but are not limited to, synthetic resins, natural rubber or latex resins and other flexible plastics or resins.

Depending upon the application and state of the orifice cavity, the level of both positive and negative pressure necessary may vary and may be controlled as described above. Applications which require minimal collection volume, and thereby maximum concentration of samples, may require correspondingly small volumes of agent delivered to the nasal passageways. The agent will primarily function to humidify orifice contents for subsequent aspiration, and may consist of a liquid spray, mist or small stream of sufficient pressure to apply the agent and humidify the orifice cavity and passageways. Conversely, applications which are not dependent upon volume or concentration considerations will not require precise pressure or volumetric control of the delivery of an agent for subsequent aspiration and testing of nasal catarrhal content.

Aspiration of orifice contents may be collected in a removable collection reservoir, either internal or external to the present device, as mentioned above. A removable second reservoir containing the tip and attached components is preferable. Alternatively, a separate reservoir or collection chamber, may also be utilized. In addition, a separate reservoir or collection chamber, whereby aspiration contents are first primed and then channeled into the collection chamber, may be utilized in applications that require sampling of orifice contents only, and not areas external or potentially contaminating the orifice sample.

In yet another embodiment, the device may be used for the purpose of diagnosis. In this form, the resultant aspirated discharge is passed through a diagnostic region contained within the device. Such a region may be prior to the collection reservoir or form a portion of the collection reservoir. Sensors may comprise a part of this diagnostic region, and may be mounted within the device prior to the second reservoir or, alternatively, included within the second reservoir. Types of sensor and/or diagnostic materials include, but are not limited to, test strips for detecting infections, pH of mucosal secretions, salt or ion values of mucosal secretions, and/or the presence of bodily agents indicating the presence of infection or other insults. Representatives of the type of sensor which may be employed has been described in U.S. Pat. No. 5,910,421, hereby incorporated in its entirety within. Bodily agents include, but are not limited to, antibodies, other immune response related materials or cells, and hormones. In addition, sensors may include electronic devices, including microelectrical mechanical systems (MEMS) devices, impedence measuring devices or optical or photonic means or devices.

Sensors may be readable as part of the device either as part of a display, window or other means of conveying the sensor or diagnostic information. Alternatively, the sensor system may be part of a subsequent assessment process, e.g. as part of a removable second reservoir which may be subsequently analyzed.

Use of the Invention in the Testing of Nasal Contents

The device may be used in the testing of orifice contents for the presence of metabolites, chemical, organic or inorganic compounds or elements, foreign particulate matter, microbial pathogens or other pathogens, organisms or compounds. In this application, delivery of an agent from a first reservoir is followed by aspiration of orifice contents from the orifice cavity and passageways. Aspirated orifice contents are collected in a removable second reservoir, after which testing of the reservoir contents is performed. The second reservoir may be contained within the tip delivery assembly, or may be contained within the aspirating assembly or external to the apparatus.

In use, the device may flush a small amount of saline or other solution into the orifice cavity of an individual. Vacuum, or negative pressure, would then be applied to draw the fluid back from the orifice cavity to sequester the sample into a cartridge for analysis. The cartridge may be removable from the device, after which a variety of assays may be performed to detect the presence of foreign particulate matter, organisms or other biochemical or chemical indices to evaluate the status or health of the individual. An example of a diagnostic assay that may be used in conjunction with the invention is in the allergy and infectious diseases diagnostic field, whereby the importance of determining the correct source of materials causing nasal and sinusitis symptoms is critical in treatment of the individual. Commercially available assays which measure pH, protein, nitrite, glucose, ketone, white blood cell esterase, bilirubin and blood may distinguish between allergies, viral infections and sinusitis, and is described in U.S. Pat. No. 5,910,421, hereby incorporated herein by reference in its entirety. Other assays which measure or detect metabolites, chemical, organic or inorganic compounds or elements, foreign particulate matter, microbial pathogens or other pathogens, organisms or compounds may also be used in conjunction with the invention, and those of ordinary skill in the art will appreciate the large variety of assays available for the detection of such compounds.

Nasal Diagnostic Device

The invention may also incorporate an assay means within the device, allowing the collection, sampling and analysis within one system. In this form, the aspirated discharge may be passed through a diagnostic region contained within the device. The diagnostic region may be part of a reservoir containing aspirated orifice contents, or may be in a separate region of the apparatus. The aspirated contents may be tested as is, or may undergo pre-treatment in preparation for analysis by the assay devices. Pre-treatment may include filtration, adjustment of pH or salinity of the contents, heat-treatment, or other treatments which aid in the assay of the orifice contents.

An example of an assay which may be used in conjunction with the invention is an assay for distinguishing between allergies, viral infections and sinusitis, disclosed in U.S. Pat. No. 5,910,421, referenced above. The patent discloses the use of commercially available strips, also referred to as dipsticks, in testing nasal secretions collected with the disclosed method. The dipsticks test for pH, protein, nitrite, glucose, ketone, white blood cell esterase, bilirubin and blood. Based on results from these test, as well as a measure of eosinophil infiltration, it may quickly be determined if a patient is suffering from an allergy, viral infection or bacterial infection.

Other assays which may be used in conjunction with the invention include immunoassays, chemical assays, biochemical assays or filtration assays to detect the presence or absence of metabolic, chemical, organic or inorganic compounds or elements, foreign particulate matter, microbial pathogens or other pathogens, organisms or compounds. Those of ordinary skill in the art appreciate the variety of assays that are available to practitioners in this field, and application of such assays to the present invention is also meant to be incorporated within the spirit and scope of this invention.

The methods described herein may be configured into devices that are patient dedicated reusable, physician reusable or that are single use throw away or sample devices. Reusable devices may be refillable and contain a cleanable, sterilizable collection volume or may contain replacement disposable components. If cross contamination is an issue then a disposable fluid path may be required with mostly disposable, sterilized components.

Use of these processes (and devices resulting from these processes) are not restricted to nasal passages. It is applicable to other body orifices and the skin surface in general. In addition, this process is suitable both for applications with humans, e.g. medical treatment and relief and for use with animals.

While the apparatus and methods in accordance with the present invention has been described, with particular reference to the illustrated embodiments, it will be understood that numerous modifications thereto will appear to those skilled in the art. Accordingly, the above description and accompanying drawings should be taken as illustrative of the invention and not in a limiting sense.

What is claimed is:

1. An apparatus for the delivery of an agent into an orifice and the subsequent aspiration of contents from the orifice, comprising:

a bulb, said bulb defining an air pocket capable of generating positive pressure when in a compressed state, and negative pressure when released from said compressed state;

a reservoir of agent;

a tube forming at least part of an agent dispensing pathway, said tube having a first end extending into said reservoir of agent;

a device tip operatively connected to said bulb at one end of the bulb and recieving a second end of said tube, said device tip having a portion configured for contacting said orifice;

a first valve positioned with respect to said air pocket, said reservoir of agent, and said tube such that said valve regulates flows through said tube in response to pressures from the compression and release of said bulb; and an aspiration pathway within said device tip comprising an aspirate chamber, wherein the aspiration pathway extends from the portion of the device tip configured for contacting said orifice to the air pocket of said bulb, and wherein the pathway is configured such that the aspirate chamber is connected to the air pocket of the bulb through a gas/liquid separator and a second valve; wherein said second valve regulates pressures and flows from the compression and release of said bulb, wherein said gas/liquid separator is positioned and configured to limit passage of aspirated contents into the air pocket of the bulb and wherein said device tip is capable of being removed from said bulb.

2. The apparatus of claim 1, wherein said gas/liquid separator comprises a filter.

3. The apparatus of claim 1, further comprising a means for delivering a metered amount of said agent to the orifice.

4. The apparatus of claim 1, further comprising a means for delaying the time between the compression and release of said bulb.

5. The apparatus of claim 1, wherein the agent is a solution.

6. The apparatus of claim 1, wherein the orifice is a nose.

7. The apparatus of claim 1, wherein the compression and release of the bulb is through a mechanical means.

* * * * *

UNITED STATES PATENT AND TRADEMARK OFFICE
CERTIFICATE OF CORRECTION

PATENT NO. : 6,907,879 B2
DATED : June 21, 2005
INVENTOR(S) : Drinan et al.

It is certified that error appears in the above-identified patent and that said Letters Patent is hereby corrected as shown below:

Title page,
Item [56], References Cited, U.S. PATENT DOCUMENTS, please delete "1/1912" and insert therefore, -- 4/1912 --.

Column 20,
Line 15, please delete "recieving" and insert therefore, -- receiving --.

Signed and Sealed this

Thirteenth Day of December, 2005

JON W. DUDAS
*Director of the United States Patent and Trademark Office*